US012599347B2

(12) United States Patent
Takahashi et al.

(10) Patent No.: US 12,599,347 B2
(45) Date of Patent: Apr. 14, 2026

(54) X-RAY IMAGING APPARATUS AND X-RAY IMAGING METHOD

(71) Applicant: FUJIFILM Healthcare Corporation, Chiba (JP)

(72) Inventors: Isao Takahashi, Chiba (JP); Kazuki Matsuzaki, Chiba (JP); Keisuke Yamakawa, Chiba (JP); Tadashi Nakamura, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 194 days.

(21) Appl. No.: 18/416,916

(22) Filed: Jan. 19, 2024

(65) Prior Publication Data

US 2024/0245369 A1      Jul. 25, 2024

(30) Foreign Application Priority Data

Jan. 23, 2023     (JP) ................................ 2023-008123

(51) Int. Cl.
　　*A61B 6/00*　　　　(2024.01)
　　*G06T 7/00*　　　　(2017.01)
(52) U.S. Cl.
　　CPC ............ *A61B 6/4452* (2013.01); *A61B 6/547* (2013.01); *G06T 7/0012* (2013.01); *G06T 2207/10116* (2013.01)
(58) Field of Classification Search
　　CPC ..... A61B 6/4452; A61B 6/547; A61B 6/4441; A61B 6/00; A61B 6/4007; A61B 6/4476; A61B 6/52; A61B 6/54; A61B 6/584; A61B 2560/0223; A61B 6/4275; A61B 6/4266; A61B 6/4021; A61B 6/12; A61B 6/06; A61B 6/5205; A61B 6/5241; A61B 6/583; A61B 6/4405; A61B 6/585; A61B 6/5264; A61B 6/032; A61B 6/587; A61B 6/5235;
(Continued)

(56) References Cited

U.S. PATENT DOCUMENTS 9,579,071 B2 *  2/2017  Lee ........................ A61B 6/022
2011/0243303 A1 * 10/2011  Vogtmeier ........... A61B 6/4007
　　　　　　　　　　　　　　　　　　　　　　378/197
(Continued)

FOREIGN PATENT DOCUMENTS

JP　　　2013173015　　　9/2013
JP　　　2021133036　　　9/2021

*Primary Examiner* — Irakli Kiknadze
(74) *Attorney, Agent, or Firm* — JCIPRNET

(57) ABSTRACT

Provided is an X-ray imaging apparatus that can understand a three-dimensional position of a treatment tool in real time during a medical operation without rotating a column of an X-ray tube.
A first X-ray tube is disposed at a position at which a target part of a subject placed on a top plate is irradiated with X-rays, and a second X-ray tube is disposed by causing the second X-ray tube to move rotationally along a circular orbit about an axis connecting the first X-ray tube and the top plate. A first X-ray image is acquired by irradiating the subject with the X-rays from the first X-ray tube. A second X-ray image is acquired by irradiating the subject with X-rays from the second X-ray tube. A position of an image of a predetermined feature part included in the first X-ray image and a position of an image of the feature part included in the second X-ray image are used to calculate a three-dimensional position of the image of the predetermined feature part.

11 Claims, 14 Drawing Sheets

(58) Field of Classification Search

CPC ....... A61B 6/08; A61B 6/5247; A61B 6/5276; A61B 6/5217; A61B 5/0295; A61B 6/503; A61B 6/504; A61B 6/481; A61B 6/03; A61B 6/469; A61B 6/507; A61B 6/463; A61B 5/029; G06T 7/0012; G06T 2207/10116; G06T 15/08; G06T 11/005; G06T 2207/30204; G06T 2207/30104; H05G 1/02; G16H 50/30

USPC ....................................... 378/4, 9, 19, 62, 92

See application file for complete search history.

(56) References Cited

U.S. PATENT DOCUMENTS

| | | | |
|---|---|---|---|
| 2018/0125438 A1* | 5/2018 | Lauritsch | G01T 1/2914 |
| 2022/0183640 A1* | 6/2022 | Ohashi | A61B 6/06 |
| 2023/0237716 A1* | 7/2023 | Manhart | G06T 11/006 |
| | | | 382/131 |

* cited by examiner

FIG. 5

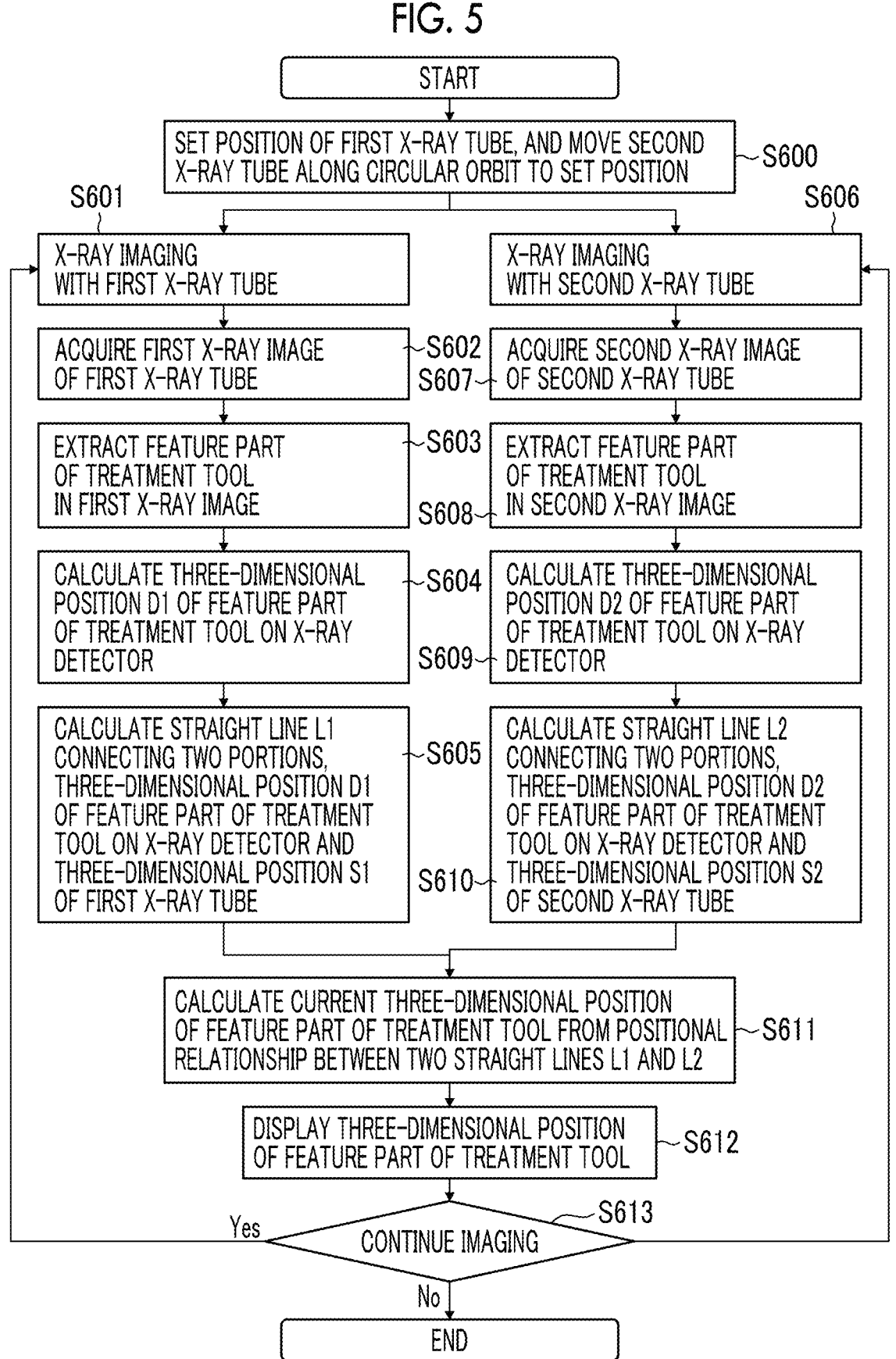

START

SET POSITION OF FIRST X-RAY TUBE, AND MOVE SECOND X-RAY TUBE ALONG CIRCULAR ORBIT TO SET POSITION — S600

S601

X-RAY IMAGING WITH FIRST X-RAY TUBE

X-RAY IMAGING WITH SECOND X-RAY TUBE — S606

ACQUIRE FIRST X-RAY IMAGE OF FIRST X-RAY TUBE — S602

S607 — ACQUIRE SECOND X-RAY IMAGE OF SECOND X-RAY TUBE

EXTRACT FEATURE PART OF TREATMENT TOOL IN FIRST X-RAY IMAGE — S603

S608 — EXTRACT FEATURE PART OF TREATMENT TOOL IN SECOND X-RAY IMAGE

CALCULATE THREE-DIMENSIONAL POSITION D1 OF FEATURE PART OF TREATMENT TOOL ON X-RAY DETECTOR — S604

S609 — CALCULATE THREE-DIMENSIONAL POSITION D2 OF FEATURE PART OF TREATMENT TOOL ON X-RAY DETECTOR

CALCULATE STRAIGHT LINE L1 CONNECTING TWO PORTIONS, THREE-DIMENSIONAL POSITION D1 OF FEATURE PART OF TREATMENT TOOL ON X-RAY DETECTOR AND THREE-DIMENSIONAL POSITION S1 OF FIRST X-RAY TUBE — S605

S610 — CALCULATE STRAIGHT LINE L2 CONNECTING TWO PORTIONS, THREE-DIMENSIONAL POSITION D2 OF FEATURE PART OF TREATMENT TOOL ON X-RAY DETECTOR AND THREE-DIMENSIONAL POSITION S2 OF SECOND X-RAY TUBE

CALCULATE CURRENT THREE-DIMENSIONAL POSITION OF FEATURE PART OF TREATMENT TOOL FROM POSITIONAL RELATIONSHIP BETWEEN TWO STRAIGHT LINES L1 AND L2 — S611

DISPLAY THREE-DIMENSIONAL POSITION OF FEATURE PART OF TREATMENT TOOL — S612

S613

Yes — CONTINUE IMAGING

No

END

X-RAY IMAGE CAPTURED WITH FIRST X-RAY TUBE DURING MEDICAL OPERATION

FIG. 13C
SECOND X-RAY IMAGE
SPINE
TUMOR
FIG. 13B
SECOND X-RAY IMAGE
SPINE
TUMOR
FIG. 13A
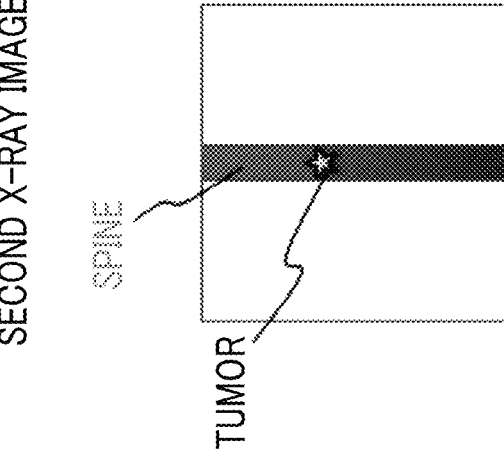
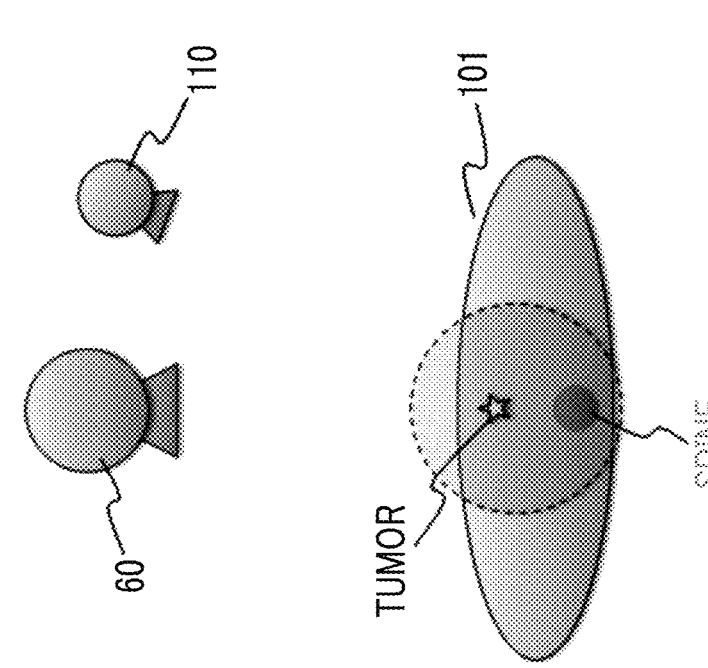
110
60
101
TUMOR
SPINE

X-RAY IMAGING APPARATUS AND X-RAY IMAGING METHOD

INCORPORATION BY REFERENCE

The present application claims priority from Japanese patent application JP-2023-008123 filed on Jan. 23, 2023, the content of which is hereby incorporated by reference into this application.

BACKGROUND OF THE INVENTION

1. Field of the Invention

The present invention relates to an X-ray imaging apparatus.

2. Description of the Related Art

A general X-ray imaging apparatus can perform X-ray imaging of a still image or X-ray imaging (so-called fluoroscopy) of a moving image by continuous imaging by irradiating a subject with X-rays from an X-ray source to detect the X-rays transmitted through the subject by a planar X-ray detector. X-ray images obtained in both the X-ray imaging and the fluoroscopy are two-dimensional projection images, and it is not possible to understand a position of a structure in the subject in a thickness direction.

Therefore, in order to enable three-dimensional imaging of the subject, for example, JP2013-173015A proposes an X-ray imaging apparatus in which a multi-X-ray generation apparatus including M×N X-ray sources and a planar detector including K×L sensors are made to face each other with an arm. This X-ray imaging apparatus can acquire any multi-layer tomographic image (so-called tomography image) by periodically performing irradiation with X-rays from the plurality of X-ray sources while rotating the arm about a slide rotation axis and a main axis, and synchronously operating the sensors, imaging a plurality of multi-directional images, and performing reconstruction based on coordinate information of the X-ray sources.

In addition, JP2021-133036A discloses a so-called biplane X-ray imaging apparatus. This X-ray imaging apparatus has a configuration in which a first X-ray tube and a first X-ray detector are disposed to face each other by a first C-type arm, and a second X-ray tube and a second X-ray detector are disposed to face each other by a second C-type arm. Rotation axes of the first C-type arm and the second C-type arm are set to intersect with each other. A three-dimensional image can be obtained by rotating each of the first C-type arm and the second C-type arm to perform imaging.

SUMMARY OF THE INVENTION

The biplane X-ray imaging apparatus in the related art as in JP2021-133036A is large and expensive. On the other hand, in a multi-tube system using the M×N X-ray sources as in JP2013-173015A, in a case in which an object to be viewed overlaps with another structure in an image captured by using one X-ray source, the switching to another X-ray source can be performed. However, since the positions of M×N X-ray sources are not significantly different from each other, a degree of freedom of position selection is not large. Therefore, it may not be possible to eliminate the overlap between the object to be viewed and another structure.

In addition, the apparatuses in JP2013-173015A and JP2021-133036A can obtain a three-dimensional image or a tomography image of the subject by rotating the arm that supports the X-ray source and the X-ray detector around the subject. However, in a case in which the three-dimensional image or the like is captured during a medical operation, an operator needs to temporarily move away from the subject in order to avoid contact with the rotating X-ray source or arm. Therefore, it is difficult to capture the three-dimensional image while inserting a surgical tool or the like.

On the other hand, in a case in which the purpose is to understand a position of a device, such as a treatment tool, the three-dimensional image or the tomography image is not always necessary. Therefore, there is a demand for a technique of understanding the position of the device without capturing the three-dimensional image or the tomography image.

An object of the present invention is to provide an X-ray imaging apparatus that can understand a three-dimensional position of a device in real time without rotating an arm that supports an X-ray tube during a medical operation.

In order to achieve the above object, an aspect of the present invention provides an X-ray imaging apparatus including a top plate on which a subject is placed, a first X-ray tube that irradiates the subject with X-rays, a first support portion that supports the first X-ray tube, a second X-ray tube that irradiates the subject with X-rays, a second support portion that supports the second X-ray tube, an X-ray detector that detects the X-rays that are applied from the first X-ray tube and the second X-ray tube and are transmitted through the subject, and an operation unit. The operation unit acquires a first X-ray image from output of the X-ray detector that has detected the X-rays applied from the first X-ray tube, acquires a second X-ray image from output of the X-ray detector that has detected the X-rays applied from the second X-ray tube, and uses a position of an image of a predetermined feature part included in the first X-ray image and a position of an image of the feature part included in the second X-ray image to calculate a three-dimensional position of the image of the predetermined feature part. The second support portion includes a mechanism that supports the second X-ray tube in a rotationally movable manner along a circular orbit about an axis connecting the first X-ray tube and the top plate.

According to the aspect of the present invention, it is possible to provide the X-ray imaging apparatus that can understand the three-dimensional position of the treatment tool in real time during a medical operation without rotating the column of the X-ray tube.

Figure 4:
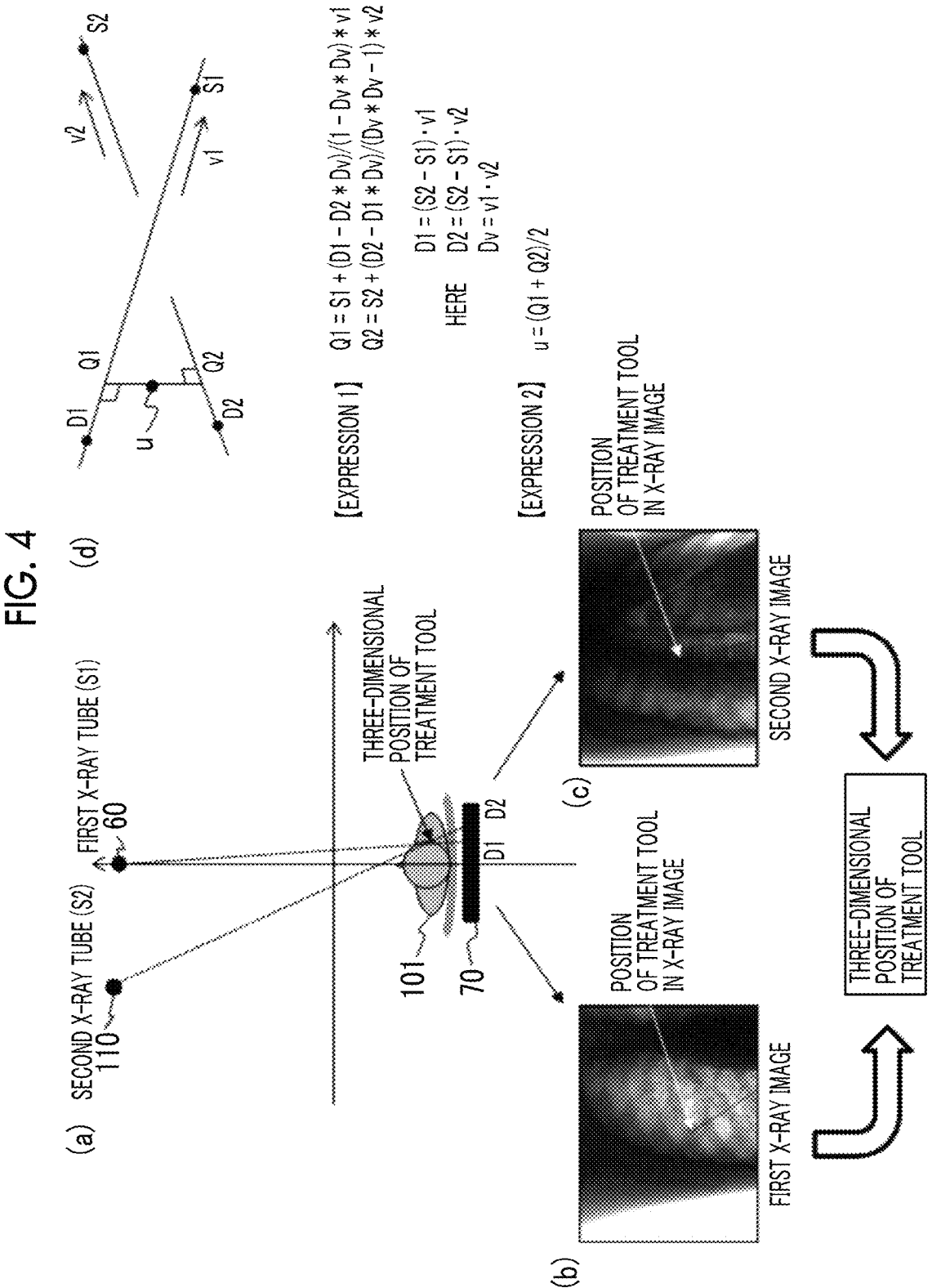

(a) of FIG. 4 is an explanatory diagram showing three-dimensional positions S1 and S2 of the first X-ray tube 60 and the second X-ray tube 110 of the X-ray imaging apparatus 1 according to Embodiment 1 and three-dimensional positions D1 and D2 of a feature part of a treatment tool projected onto the X-ray detector 70, (b) of FIG. 4 is a diagram showing an example of a first X-ray image, (c) of FIG. 4 is a diagram showing an example of a second X-ray image, and (d) of FIG. 4 is a diagram showing a calculation method of the three-dimensional position of the feature part of the treatment tool.

FIG. 5 is a flowchart showing an operation of the X-ray imaging apparatus 1 according to Embodiment 1.

Figure 6:
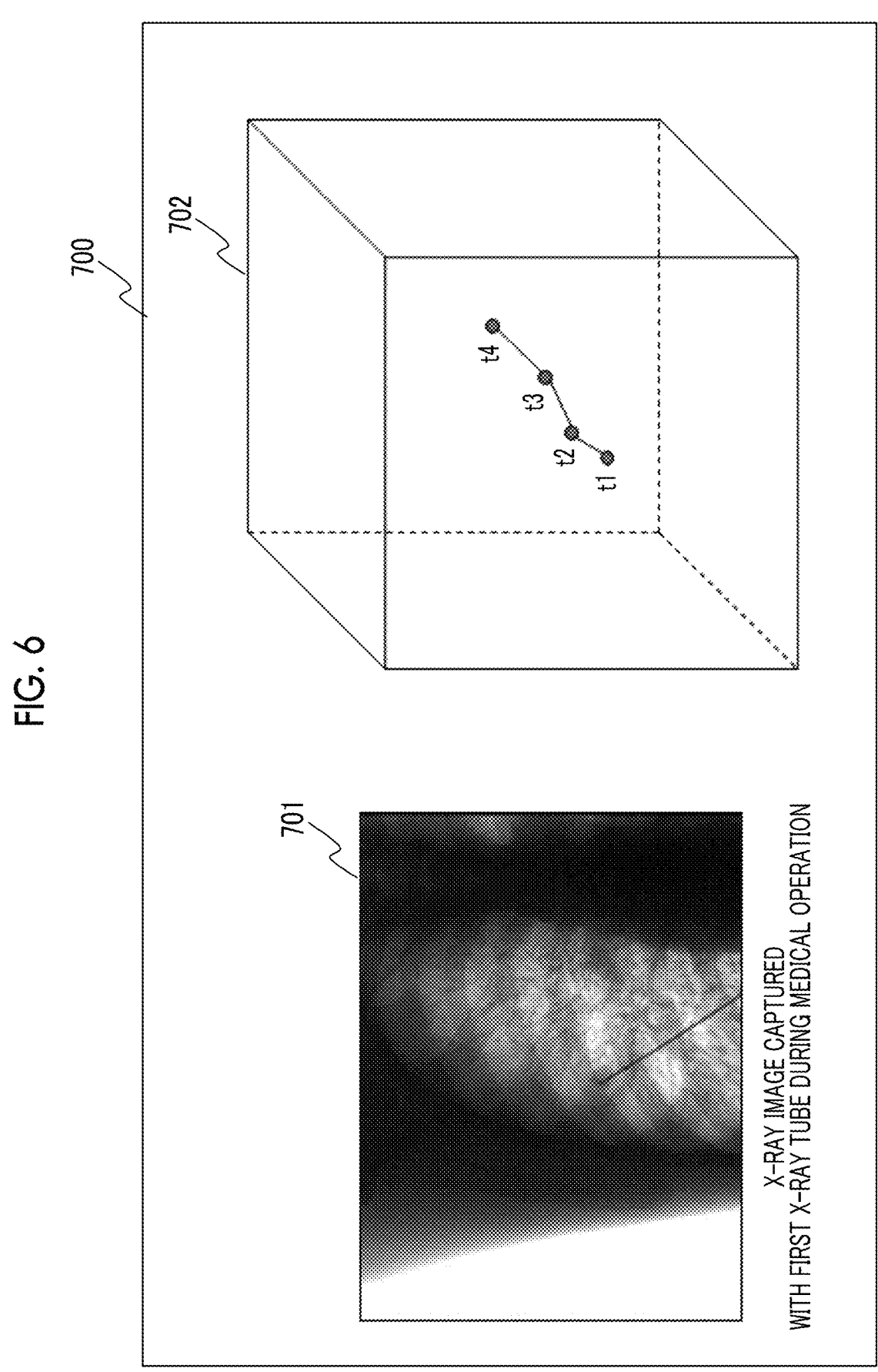

FIG. 6 is a diagram showing an example of a screen displayed on a display unit of the X-ray imaging apparatus 1 according to Embodiment 1.

Figure 7:
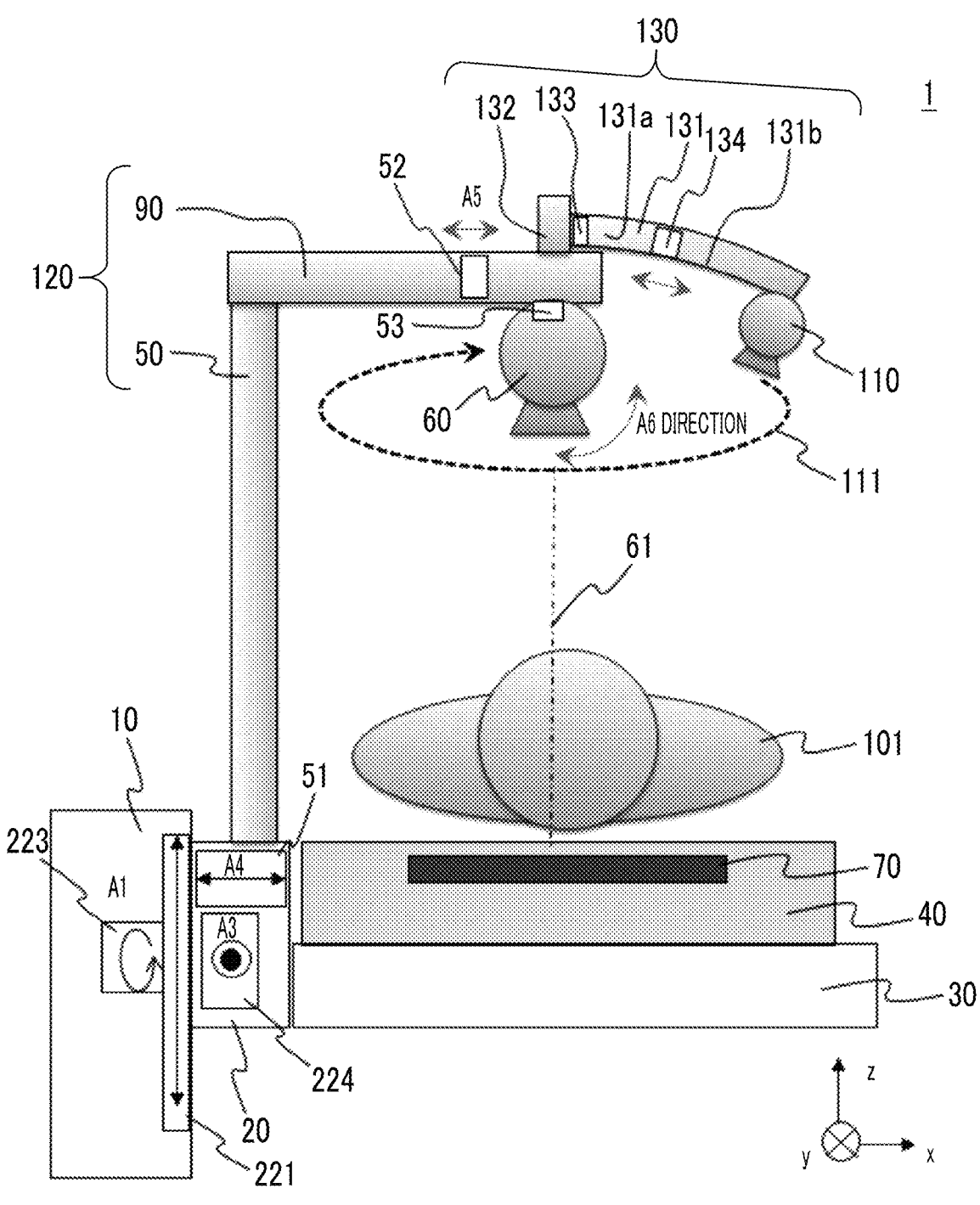

FIG. 7 is a block diagram showing disposition and a movement direction of two X-ray tubes in a case in which an X-ray imaging apparatus 1 according to Embodiment 2 is viewed from a side surface.

Figure 8:
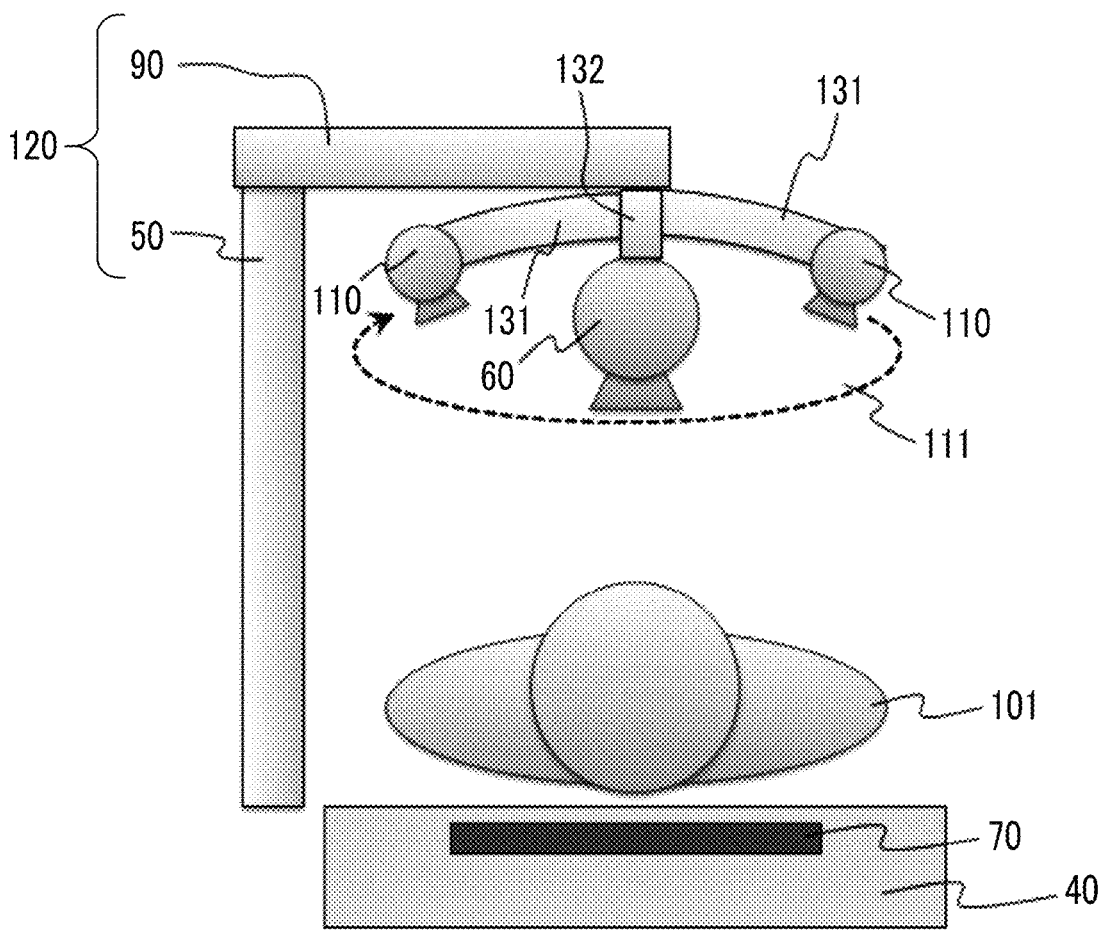

FIG. 8 is a block diagram showing disposition and a movement direction of two X-ray tubes in a case in which an X-ray imaging apparatus 1 according to Embodiment 3 is viewed from a side surface.

Figure 9:
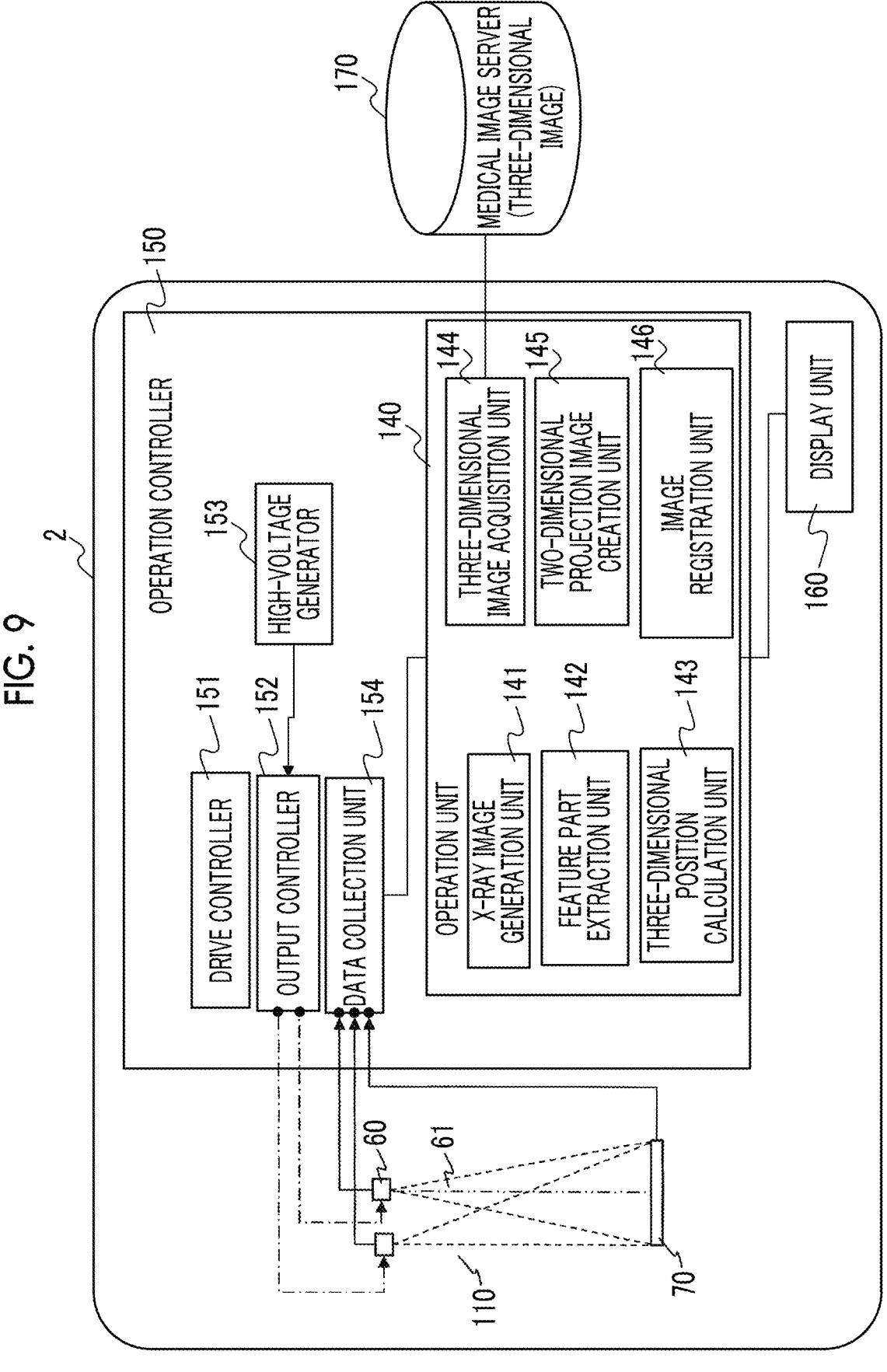

FIG. 9 is a block diagram showing a configuration of main units of an X-ray imaging apparatus 2 according to Embodiment 4.

Figure 10:
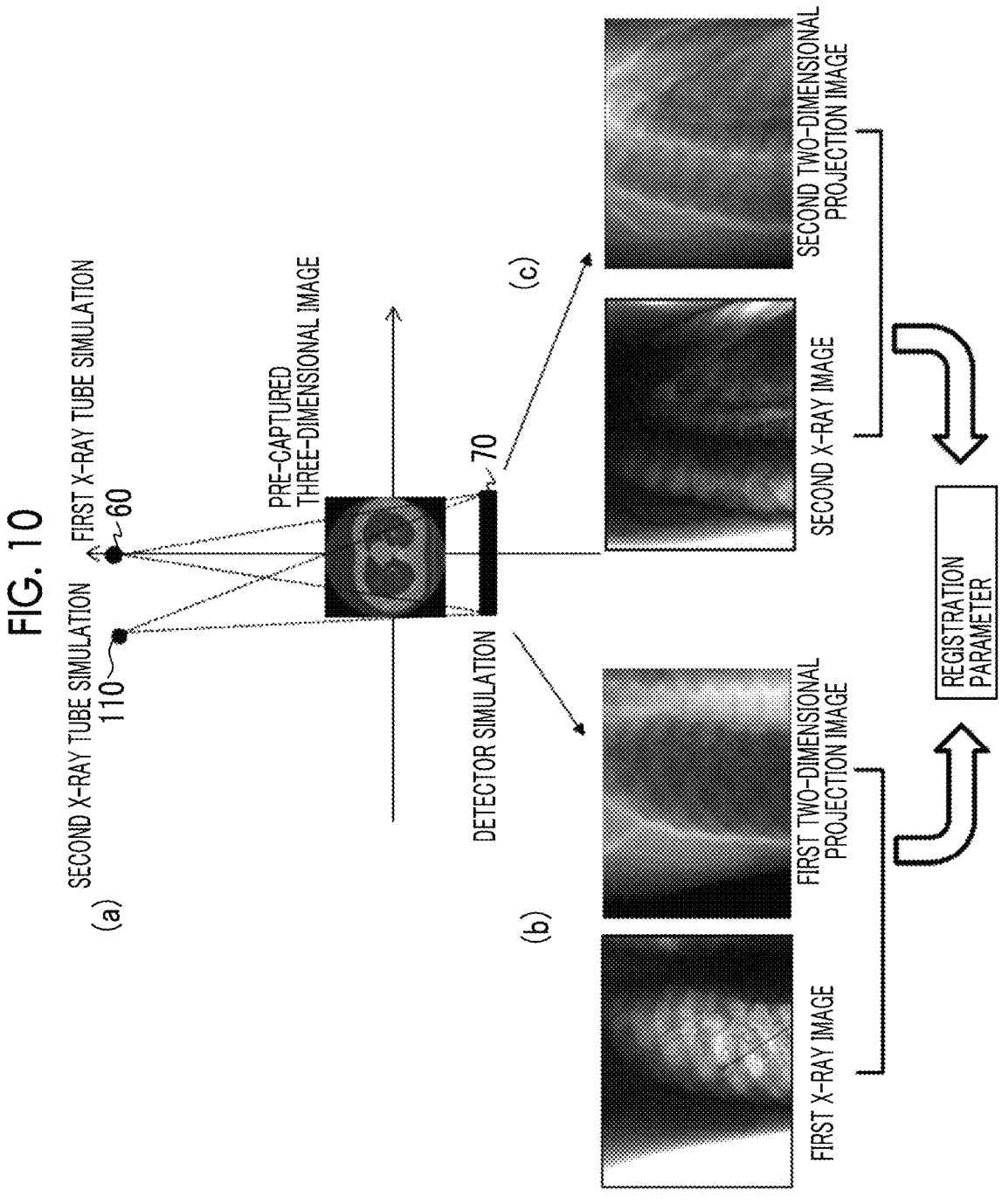

(a) of FIG. 10 is an explanatory diagram showing calculation of a two-dimensional projection image by projecting a pre-captured three-dimensional image acquired by the X-ray imaging apparatus 2 according to Embodiment 4, (b) of FIG. 10 is a diagram showing an example of a first two-dimensional projection image and a first X-ray image, and (c) of FIG. 10 is a diagram showing an example of a second two-dimensional projection image and a second X-ray image.

Figure 11:
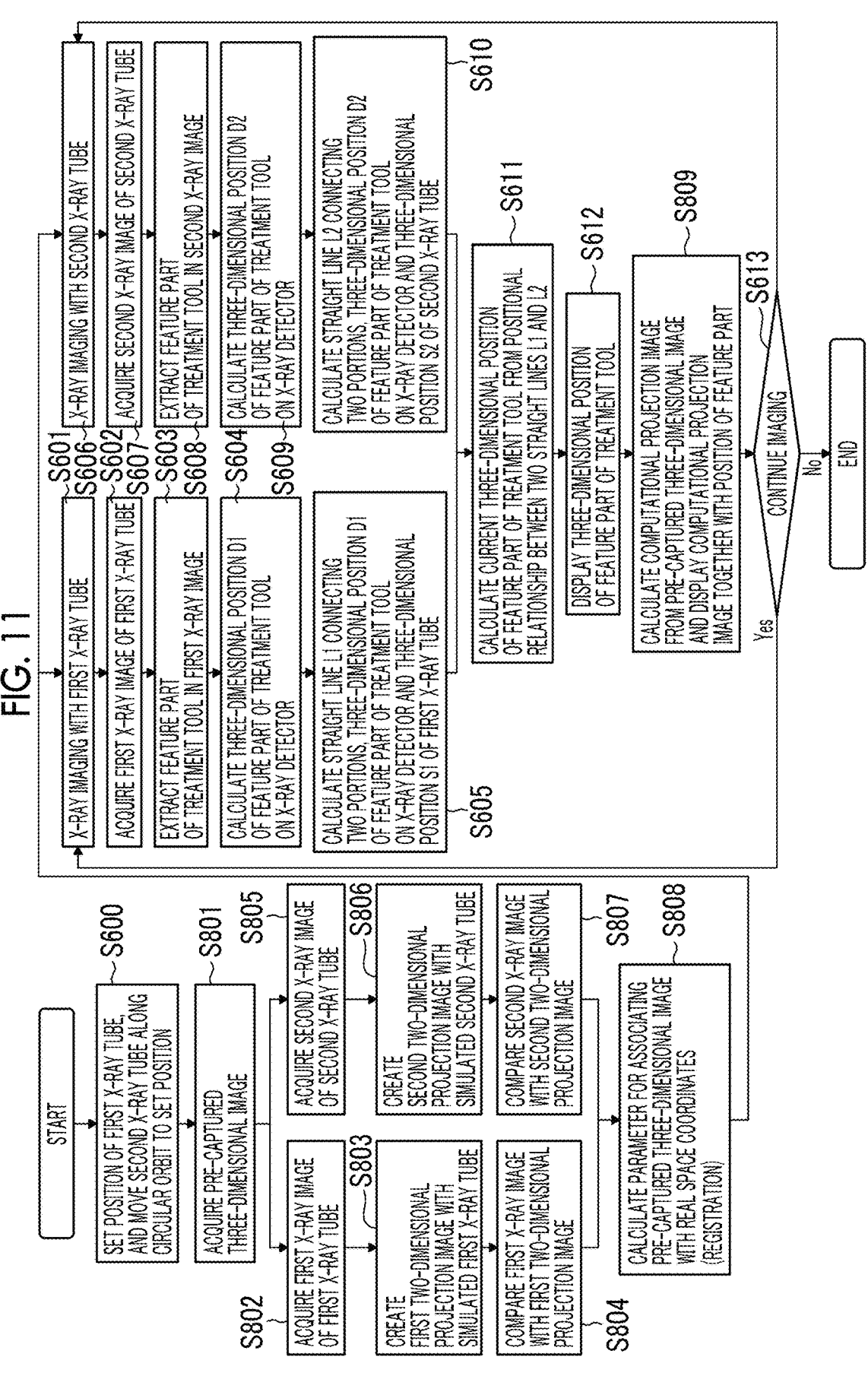

FIG. 11 is a flowchart showing an operation of the X-ray imaging apparatus 2 according to Embodiment 4.

Figure 12:
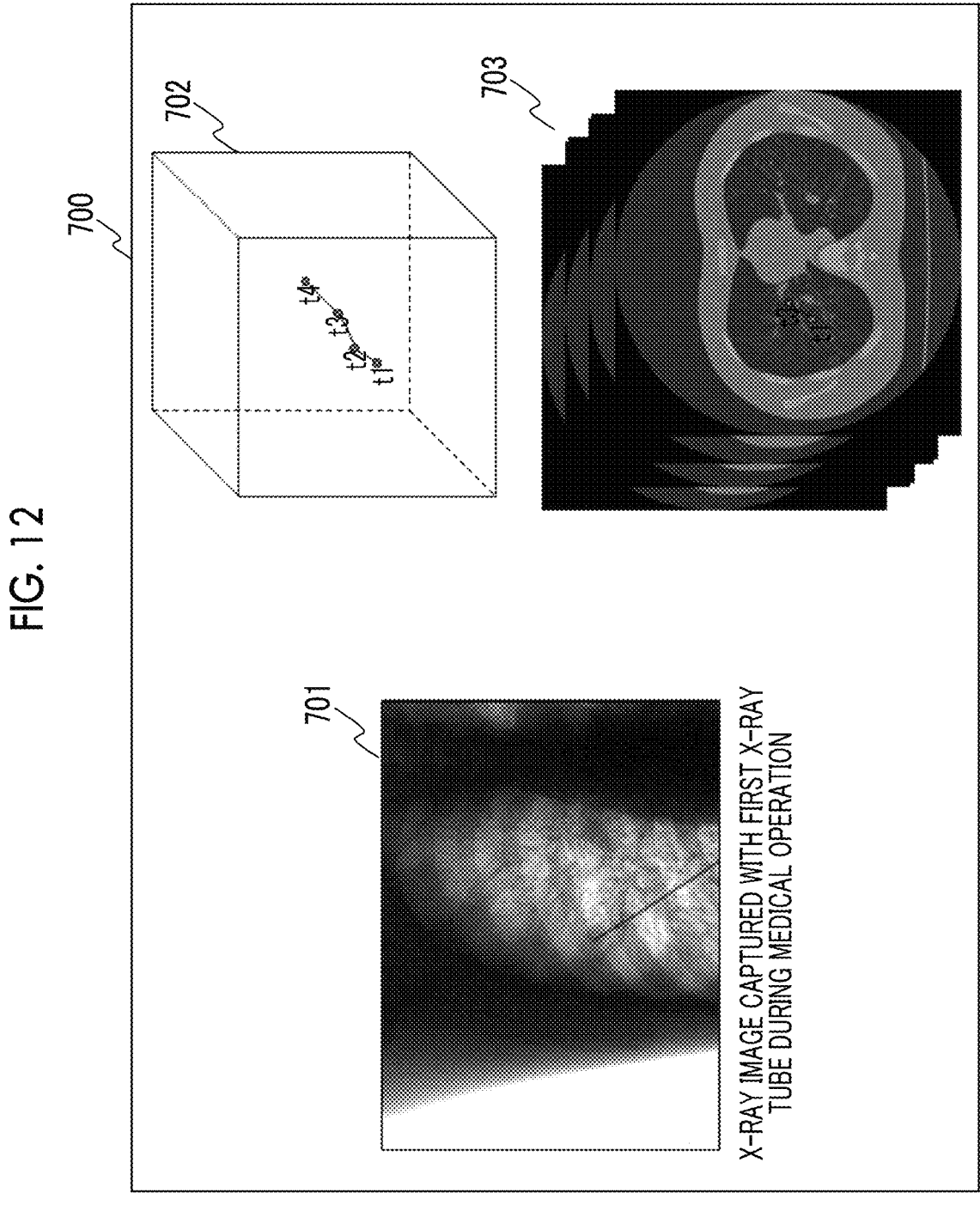

FIG. 12 is a diagram showing an example of a screen displayed on a display unit of the X-ray imaging apparatus 2 according to Embodiment 4.

FIG. 13A is a diagram showing a positional relationship between a tumor and a spine of a subject 101 with respect to a first X-ray tube 60 and a second X-ray tube 110 of the X-ray imaging apparatus according to Embodiment 5, and FIGS. 13B and 13C are diagrams showing a second X-ray image according to Embodiment 5.

Figures 14A, 14B, 14C:
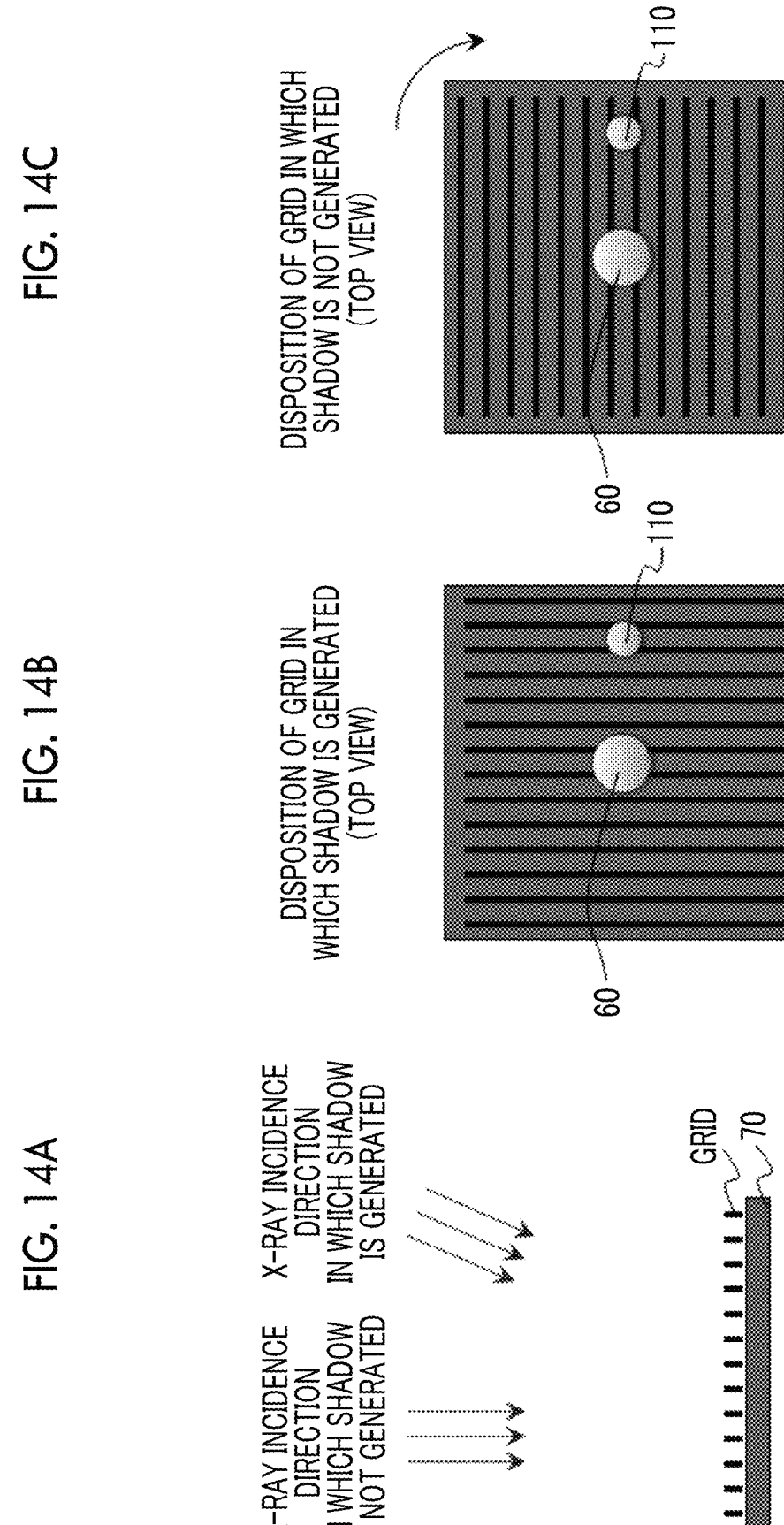

FIG. 14A is a diagram showing a relationship between a grid and an incidence direction of X-rays in Embodiment 7, FIG. 14B is a diagram showing disposition in which an optical axis of a second X-ray tube 110 and a direction of rows of the grid intersect with each other, and FIG. 14C is a diagram showing disposition in which the optical axis of the second X-ray tube 110 and the direction of the rows of the grid are parallel to each other.

DESCRIPTION OF THE PREFERRED EMBODIMENTS

Hereinafter, embodiments of the present invention will be described with reference to the accompanying drawings.

Embodiment 1

A configuration of an X-ray imaging apparatus 1 according to the embodiment will be described.

Figure 1:
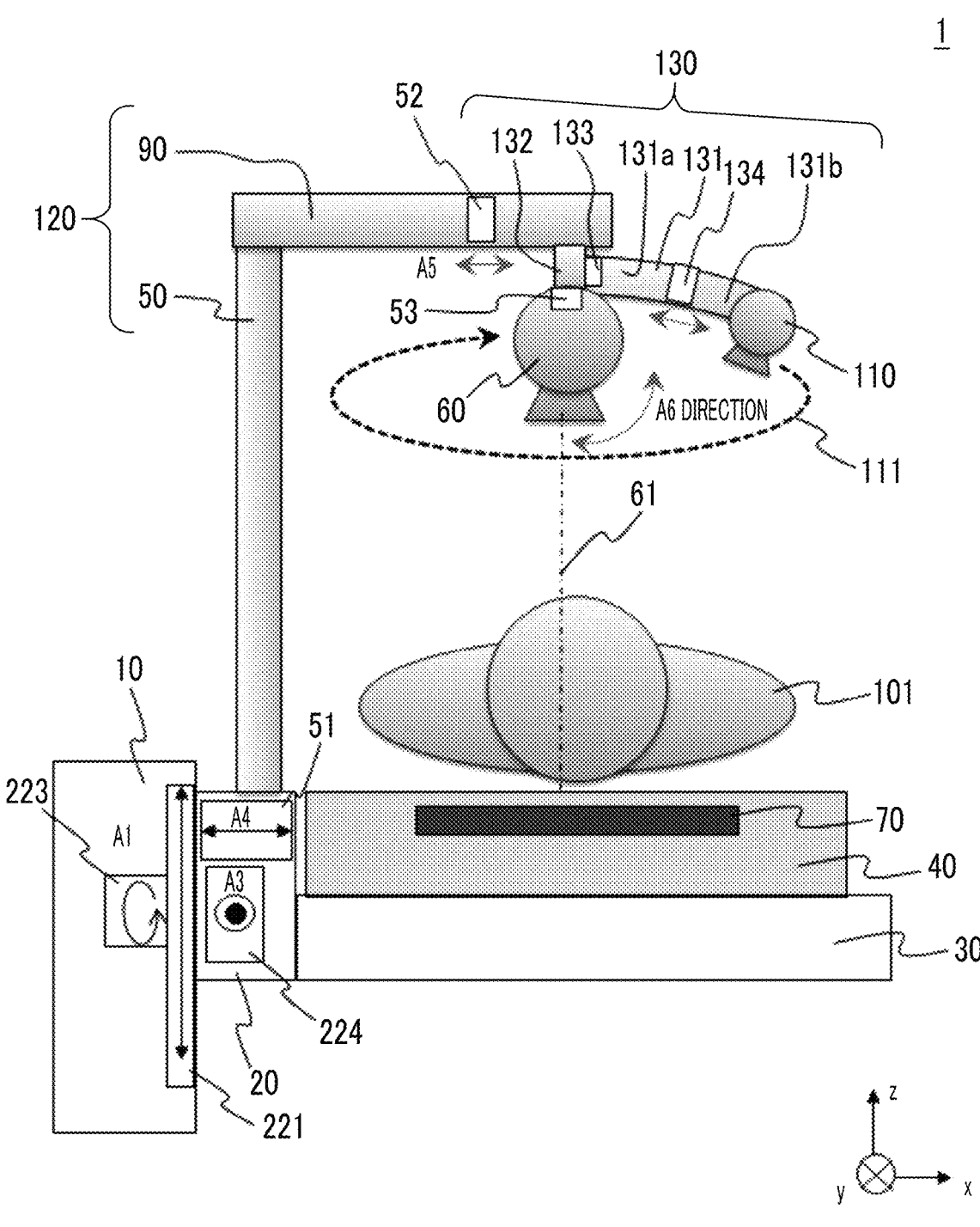
FIG. 1 is a block diagram showing disposition and a movement direction of two X-ray tubes in a case in which an X-ray imaging apparatus 1 according to Embodiment 1 of the present invention is viewed from a side surface.
Figure 2:
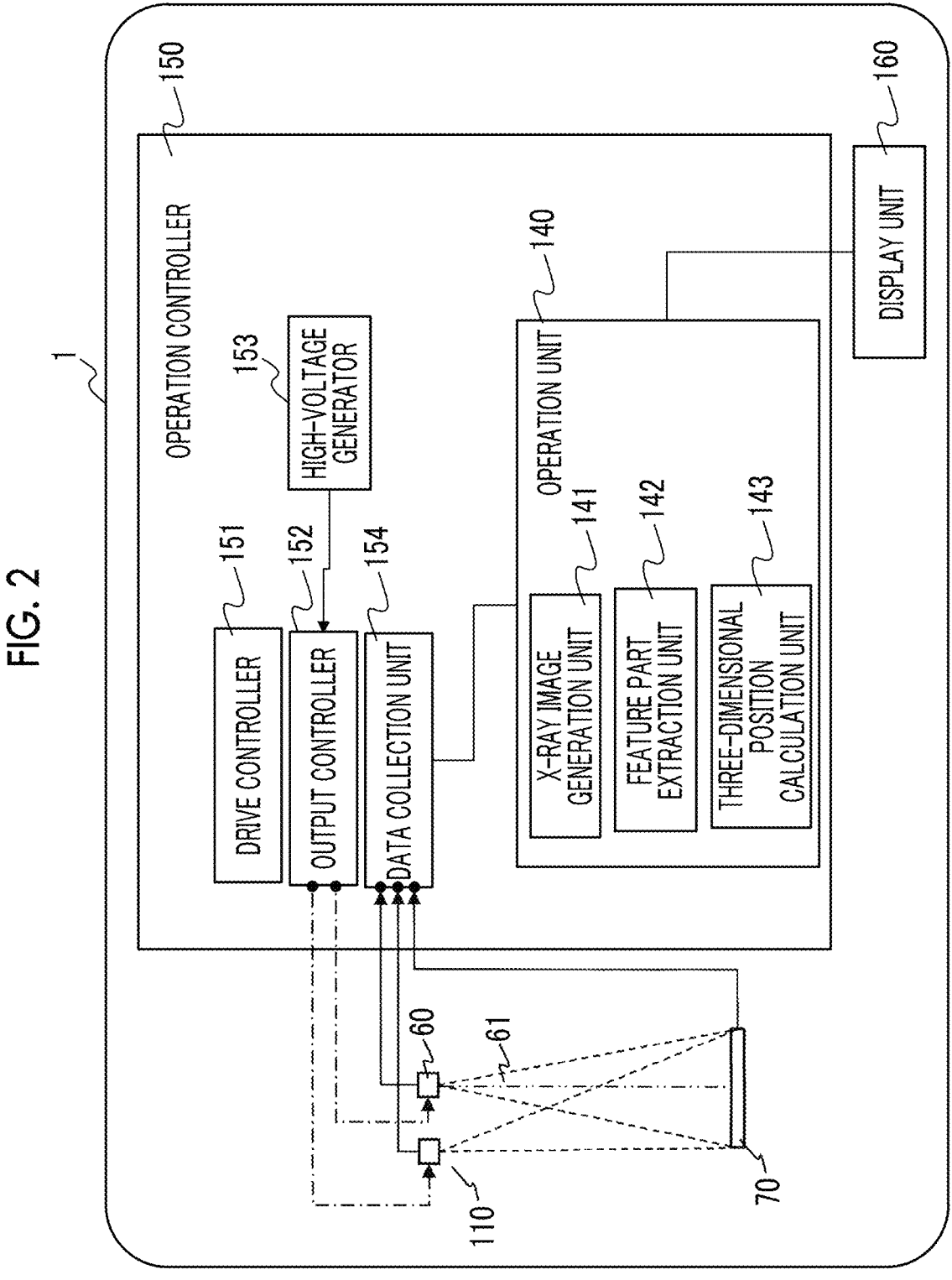
FIG. 2 is a block diagram showing a configuration of main units of the X-ray imaging apparatus 1 according to Embodiment 1.
Figure 3:
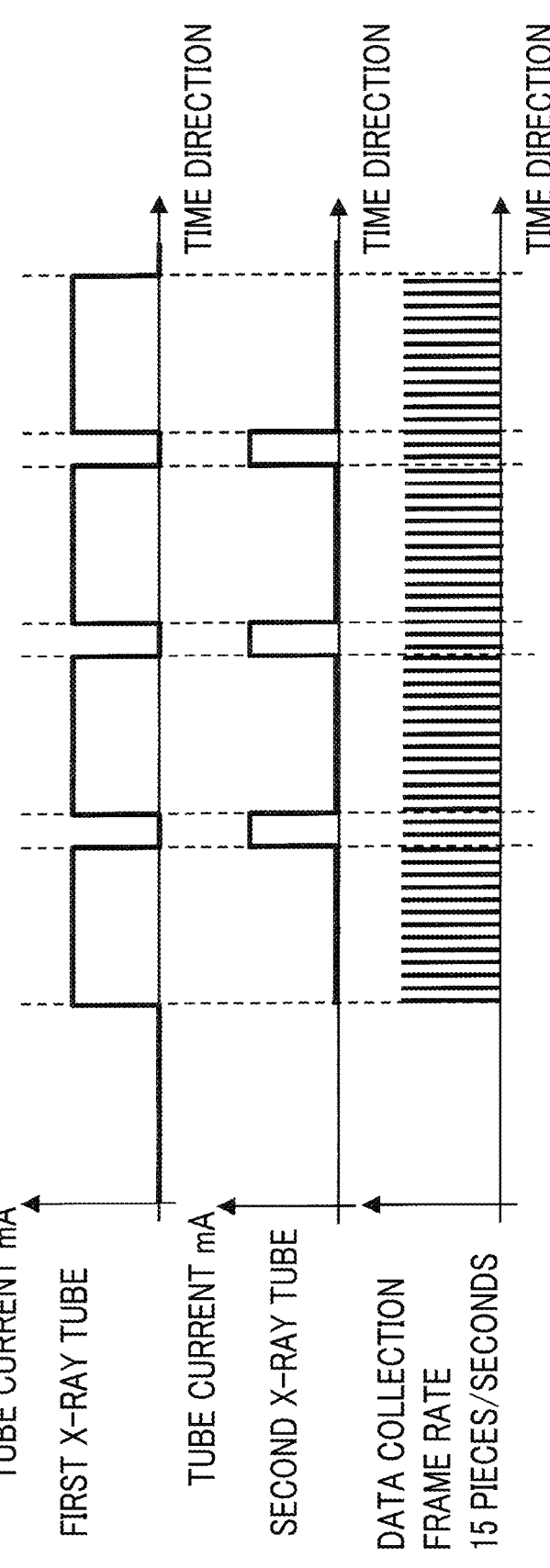
FIG. 3 is a timing chart showing a timing of supplying a tube current to a first X-ray tube 60 and a second X-ray tube 110 of the X-ray imaging apparatus 1 according to Embodiment 1 and a timing of data collection from an X-ray detector.

FIG. 1 is a diagram showing disposition and a movement direction of two X-ray tubes in a case in which the X-ray imaging apparatus 1 is viewed from a side surface. FIG. 2 is a block diagram showing a configuration of main units of the X-ray imaging apparatus 1. FIG. 3 is a diagram showing a timing of supplying a tube current to the two X-ray tubes and a timing of data collection from an X-ray detector.

As shown in FIGS. 1 and 2, the X-ray imaging apparatus 1 comprises a top plate 40 on which a subject is placed, and a first X-ray tube 60 and a second X-ray tube 110 that irradiate the subject with X-rays. The first X-ray tube 60 is supported by a first support portion 120. The second X-ray tube 110 is supported by a second support portion 130. The X-rays applied from the first X-ray tube 60 and the second X-ray tube 110 are transmitted through a subject 101. An X-ray detector 70 is disposed in the top plate 40 at a position irradiated with the X-rays transmitted through the subject 101.

The first support portion 120 includes a column 50 supported by a stand 10, and a first X-ray support arm 90.

The second support portion 130 includes a mechanism that supports the second X-ray tube 110 in a rotationally movable manner along a circular orbit 111 about an axis 61 connecting the first X-ray tube 60 and the top plate 40. The axis 61 may or may not be matched with an optical axis of the first X-ray tube 60. In a case in which the first X-ray tube 60 comprises a swing mechanism that is rotationally movable in any direction at a connecting portion with the first support portion 120, the axis 61 and the optical axis of the first X-ray tube 60 may be not match.

A specific structural example of the second support portion 130 will be described with reference to FIG. 1. The second support portion 130 includes an arm 131, a support shaft 132, and a rotation mechanism 133. The support shaft 132 is provided at a position at which the first X-ray tube 60 of the first support portion 120 is supported. Here, the support shaft 132 has a structure in which the support shaft 132 is provided below a distal end of the first X-ray support arm 90 of the first support portion 120, and the first X-ray tube 60 is supported by a lower end of the support shaft 132.

The arm 131 has a base 131a and a distal end, and the base 131a is supported by the support shaft 132. The rotation mechanism 133 is a mechanism that causes the base 131a of the arm 131 to move rotationally about the support shaft 132. For example, the rotation mechanism 133 can have a configuration in which a guide rail that is provided along a circumferential direction of an outer periphery of the support shaft 132 and an engaging part that is provided at the base 131a of the arm 131 and that is engaged with the guide rail are provided. With such a configuration, the arm 131 can be caused to move rotationally along the outer periphery of the support shaft 132. The second X-ray tube 110 is supported at a distal end 131b of the arm 131. As a result, the second X-ray tube 110 can be rotated around the first X-ray tube 60 along the circular orbit 111 about the axis 61.

In addition, although the user may manually rotate the second X-ray tube 110 along the circular orbit 111, the second support portion 130 may be provided with a driving unit that changes the position of the second X-ray tube 110 along the circular orbit 111. For example, by forming the guide rail of the rotation mechanism 133 into a rack structure, disposing a pinion that meshes with the rack structure at the engaging part, and disposing a motor that rotates the pinion as a driving unit, the second X-ray tube 110 can be rotated and moved along the circular orbit 111 by a rotation amount of the motor.

The second support portion 130 may be provided with a stopper that switches the second X-ray tube 110 from a state in which the second X-ray tube 110 is rotatable along the circular orbit 111 to a state in which the second X-ray tube 110 is fixed. For example, a protrusion that is able to appear and disappear and provided around the support shaft 132 can be used as a stopper. By causing the protrusion to protrude, the rotation of the arm 131 is prevented, so that the second X-ray tube 110 can be fixed.

Further, a configuration can also be adopted in which the second support portion 130 comprises a mechanism unit that changes a radius of the circular orbit 111. For example, an expansion and contraction mechanism 134 that causes the arm 131 to be expanded and contracted is disposed in the arm 131. Specifically, a slide rail mechanism can be used as the expansion and contraction mechanism 134. As a result, the arm 131 can be expanded and contracted to a desired length, and the radius of the circular orbit 111 can be changed.

In addition, by forming the arm 131 in a curved shape as shown in FIG. 1, a relationship between a height of the first X-ray tube 60 and a height of the circular orbit 111 of the second X-ray tube 110 can be made to a desired relationship. For example, as shown in FIG. 1, the height of the circular orbit 111 of the second X-ray tube 110 can be made to be substantially the same as the height of the first X-ray tube 60.

The configuration of the second support portion 130 is not limited to the above-described structure, need only be any configuration as long as the second X-ray tube 110 can be rotated along the circular orbit 111, and may be a configuration in which the second support portion 130 is directly installed upright on the stand 10.

In this way, by forming a structure that is rotationally movable around the first X-ray tube 60 along the circular orbit 111 of the second X-ray tube 110, even in a case in which the feature part (for example, the distal end of the treatment tool, such as the catheter) of which the position in the subject 101 is to be detected in the image captured by the second X-ray tube 110 overlaps with a structure, such as a bone, of the subject 101 and the image of the feature part cannot be understood on the image, it is possible to perform the imaging from different angles by causing the second X-ray tube 110 to move rotationally, and it is possible to detect the position of the feature part.

A configuration for performing the control and the operation of the X-ray imaging apparatus 1 will be described. As shown in FIG. 2, the X-ray imaging apparatus 1 includes an operation controller 150, and an operation unit 140, a drive controller 151, an output controller 152, a data collection unit 154, and a high-voltage generator 153 are disposed in the operation controller 150.

The operation unit 140 comprises an X-ray image generation unit 141, a feature part extraction unit 142, and a three-dimensional position calculation unit 143. The X-ray image generation unit 141 acquires a first X-ray image from output of the X-ray detector 70 that has detected the X-rays applied from the first X-ray tube 60, acquires a second X-ray image from output of the X-ray detector 70 that has detected the X-rays applied from the second X-ray tube 110. The feature part extraction unit 142 extracts a position of an image of a predetermined feature part included in the first X-ray image and a position of an image of the feature part included in the second X-ray image. The three-dimensional position calculation unit 143 calculates the three-dimensional position of the image of the predetermined feature part from the extraction result of the feature part extraction unit 142.

A maximum irradiation region of the X-rays from the second X-ray tube 110 to the X-ray detector 70 may be smaller than a maximum irradiation region of the X-rays from the first X-ray tube 60 to the X-ray detector 70.

In addition, maximum output of the X-rays of the second X-ray tube 110 may be smaller than maximum output of the X-rays of the first X-ray tube 60.

A second slide mechanism 52 that moves a position of the first X-ray tube 60 in the width direction (A5 direction=x direction) of the top plate 40 is provided in the first X-ray support arm 90 of the first support portion 120 that supports the first X-ray tube 60. Here, since the support shaft 132 and the second X-ray tube 110 are also supported by the first X-ray support arm 90, the second X-ray tube 110 also moves together with the first X-ray tube 60.

Further, a first rotation mechanism 53 that causes the first X-ray tube 60 to move rotationally (in A6 direction) about an axis parallel to the major axis (y axis) of the top plate 40 at a distal end of the first X-ray support arm 90 (in FIG. 1, a lower end of the support shaft 132) is disposed at a connecting portion between the first X-ray tube 60 and the support shaft 132.

In addition, in the present embodiment, the column 50 of the first support portion 120 is mounted on the column support arm 20 provided on the stand 10. A first slide mechanism 51 that moves a lower end of the column 50 in the width direction (A4 direction=x direction) of the top plate 40 with respect to the stand 10 is provided between the lower end of the column 50 of the first support portion 120 and the column support arm 20. The first slide mechanism 51 integrally moves the first support portion 120 and the second support portion 130 in the x direction.

A support frame 30 that supports the top plate 40 is mounted on the column support arm 20 in addition to the first support portion 120. The stand 10 has a built-in drive mechanism 221 that moves the column support arm 20 up and down (A1 direction=z axis). As a result, the top plate 40, the first X-ray tube 60, and the second X-ray tube 110 can be moved up and down while maintaining the positional relationship between the first X-ray tube 60 and the top plate 40.

In addition, the column support arm 20 of the stand 10 has a built-in moving mechanism 224 that moves the first support portion 120 in the major axis direction (A3 direction=y axis) of the top plate 40. As a result, the first X-ray tube 60 and the second X-ray tube 110 can be moved with respect to the top plate 40 in the major axis direction (y axis) of the top plate 40.

In addition, the stand 10 comprises a raising and laying mechanism 223 that rotates the column support arm 20 (in A9 direction) with the central axis (x axis) of the column support arm 20 as a rotation center. As a result, the top plate 40 can be raised and laid while maintaining the positional relationship between the first X-ray tube 60 and the top plate 40.

Further, a connecting portion between the column support arm 20 and the first support portion 120 comprises an inclination mechanism (not shown) that causes the first support portion 120 to move rotationally with the central axis (x axis) of the column support arm 20 as a rotation center with respect to the column support arm 20 along a semi-circular rail. As a result, the first support portion 120 can be inclined with respect to the top plate 40 with the x axis as a rotation center.

Further, although not shown, a drive mechanism (not shown) that moves the X-ray detector 70 in the major axis direction and a minor axis direction of the top plate 40 with respect to the top plate 40 is provided in the top plate 40.

Each of the drive mechanisms 51 to 53, 133 to 134, 221, and 223 to 224 may have any configuration. As an example, a configuration can be adopted in which a rack disposed along the movement direction, a pinion that meshes with the rack, and a motor that rotates the pinion are provided.

The operation controller 150 comprises a drive controller 151 that controls the operation of each of the drive mechanisms 51 to 53, 133 to 134, 221, and 223 to 224, an output controller 152, a high-voltage generator 153, a data collection unit 154, and an operation unit 140.

The output controller 152 supplies a high-voltage generated by the high-voltage generator 153 to the first X-ray tube 60 and the second X-ray tube 110 with set voltage value and current value at timings as shown in FIG. 3, respectively, and applies the X-rays from the first X-ray tube 60 and the second X-ray tube 110. The output controller 152 can individually control the output of the first X-ray tube 60 and the output of the second X-ray tube 110.

The data collection unit 154 collects signals output by X-ray detection elements two-dimensionally arranged in the X-ray detector 70 in response to the irradiation with the X-rays at the timings shown in FIG. 3. In addition, the data collection unit 154 acquires information on the start and end of the irradiation from each X-ray tube from the tube current and the tube voltage that are controlled by the output controller 152.

As described above, the operation unit 140 comprises an X-ray image generation unit 141, a feature part extraction unit 142, and a three-dimensional position calculation unit 143. The X-ray image generation unit 141 receives the output of the X-ray detector 70 that has detected the X-rays applied from the first X-ray tube, from the data collection unit 154, to generate a first X-ray image (see (b) of FIG. 4). In addition, the X-ray image generation unit 141 receives the output of the X-ray detector 70 that has detected the X-rays applied from the second X-ray tube, from the data collection unit 154, to generate a second X-ray image (see (c) of FIG. 4).

The feature part extraction unit 142 extracts a position of an image of a predetermined feature part included in the first X-ray image and a position of an image of the feature part included in the second X-ray image by a known method. The feature part is, for example, a distal end of a treatment tool, such as a catheter.

The three-dimensional position calculation unit 143 uses the position of the image of the predetermined feature part included in the first X-ray image and the position of the image of the feature part included in the second X-ray image calculates a three-dimensional position of the predetermined feature part.

An example of a specific calculation method of the feature part will be described. As shown in (a) of FIG. 4, a three-dimensional position (real space coordinates) of the first X-ray tube 60 is denoted by S1, a three-dimensional position (real space coordinates) of the feature part in the first X-ray image is denoted by D1, and a straight line connecting S1 and D1 is denoted by L1. In addition, a three-dimensional position of the second X-ray tube 110 is denoted by S2, a three-dimensional position of the feature part in the second X-ray image is denoted by D2, and a straight line connecting S2 and D2 is denoted by L2. The same feature part such as the distal end of the treatment tool are projected onto D1 and D2. Therefore, the straight lines L1 and L2 ideally intersect with each other at one point as shown in (a) of FIG. 4. Actually, as shown in (d) of FIG. 4, there are cases where the straight lines L1 and L2 do not intersect with each other due to a measurement error or the like. Therefore, a point Q1 on the straight line S1-D1 and a point Q2 on the straight line S2-D2 where the distance between the two straight lines is closest are obtained, and for example, a midpoint u of the two points can be set as the position of the image of the feature part.

The points Q1 and Q2 shown in (d) of FIG. 4 can be obtained according to Expression 1.

$$Q1 = S1 + (D1 - D2 * Dv)/(1 - Dv * Dv) * v1 \qquad (1)$$

$$Q2 = S2 + (D2 - D1 * Dv)/(Dv * Dv - 1) * v2$$

$$\text{Here, } D1 = (S2 - S1)v1$$

$$D2 = (S2 - S1)v2$$

$$Dv = v1 \cdot v2$$

From the three-dimensional positions of the points Q1 and Q2 obtained by Expression 1, the three-dimensional position u of the feature part can be calculated by using Expression 2.

$$u = (Q1 + Q2)/2 \qquad (2)$$

Next, the operation of each unit in a case in which the three-dimensional position of the distal end of the treatment tool (device) is detected during the medical operation under an X-ray fluoroscopic image by the X-ray imaging apparatus 1 according to the present embodiment will be described with reference to the flow of FIG. 5.

Step S600

The subject 101 is placed on the top plate 40, and a user operates each of the drive mechanisms 51 to 53, 221, and 223 to 224 under the control of the drive controller 151, to dispose the first X-ray tube 60 at a position at which a target part into which the device is inserted can be imaged. In addition, based on prior information of the target part and/or the device to be used, the user moves the second X-ray tube 110 along the circular orbit 111 by the mechanisms 133 and 134, disposes the second X-ray tube 110 at a position at which the distal end of the device to be inserted can be imaged in a direction that does not overlap with a bone, such as a spine, or an organ, such as a liver. In this case, a distance between the first X-ray tube 60 and the second X-ray tube 110 may be adjusted by adjusting a length of the arm 131 by the expansion and contraction mechanism 134.

Step S601

In a case in which the operator gives an instruction to start the operation, as shown in FIG. 3, the tube current is supplied to the first X-ray tube 60 and the subject 101 is irradiated with the X-rays from the first X-ray tube 60, to start X-ray imaging.

Step S602

The X-ray image generation unit 141 acquires an X-ray image from the X-rays applied from the first X-ray tube 60.

Specifically, the X-rays that are applied from the first X-ray tube 60 and are transmitted through the subject 101 are detected by the X-ray detector 70, and the output of the X-ray detector 70 is collected by the data collection unit 154 at a timing shown in FIG. 3.

The X-ray image generation unit 141 receives the output of the X-ray detector 70 from the data collection unit 154, to generate the first X-ray image (see (b) of FIG. 4). The X-ray image generation unit 141 displays the first X-ray image on a display unit 160.

The operator inserts the treatment tool (catheter or the like) into the subject while viewing the first X-ray image on the display unit 160.

Step S603

The feature part extraction unit 142 performs image processing on the first X-ray image generated in step S602 to extract the feature part of the treatment tool (for example, the distal end of the treatment tool) in the first X-ray image.

Step S604

The three-dimensional position calculation unit 143 calculates the three-dimensional position D1 (real space coordinates) on the X-ray detector 70 onto which the feature part of the treatment tool is projected, based on the position of the treatment tool in the first X-ray image.

Step S605

The three-dimensional position calculation unit 143 calculates the straight line L1 connecting the two points, the three-dimensional position D1 (real space coordinates) of the feature part of the treatment tool on the X-ray detector and the three-dimensional position S1 (real space coordinates) of the first X-ray tube 60.

Step S606

As shown in FIG. 3, at a timing at which the irradiation with the X-rays from the first X-ray tube 60 ends, the subject 101 is irradiated with the X-rays from the second X-ray tube 110 to perform the X-ray imaging.

Specifically, the output controller 152 stops the supply of the tube current and the tube voltage to the first X-ray tube 60, supplies the tube current and the tube voltage, which are set by the operator, to the second X-ray tube 110, and performs the irradiation with the X-rays only for a predetermined time.

Step S607

The X-ray image generation unit 141 acquires an X-ray image from the X-rays applied from the second X-ray tube 110.

Specifically, the X-rays that are applied from the second X-ray tube 110 and are transmitted through the subject 101 are detected by the X-ray detector 70, and the output of the X-ray detector 70 is collected by the data collection unit 154 at a predetermined timing shown in FIG. 3.

The X-ray image generation unit 141 receives the output of the X-ray detector 70 from the data collection unit 154, to generate the second X-ray image (see (c) of FIG. 4).

As a result, the operator can check the second X-ray image captured from an angle different from an angle of the first X-ray image on the display unit 160.

Step S608

The feature part extraction unit 142 performs image processing on the second X-ray image generated in step S607 to extract the feature part of the treatment tool (the distal end of the treatment tool) in the second X-ray image.

Step S609

The three-dimensional position calculation unit 143 calculates the three-dimensional position D2 (real space coordinates) on the X-ray detector 70 onto which the feature part of the treatment tool is projected, based on the position of the treatment tool in the second X-ray image.

Step S610

The three-dimensional position calculation unit 143 calculates the straight line L2 connecting the two points, the three-dimensional position D2 (real space coordinates) of the feature part of the treatment tool on the X-ray detector and the three-dimensional position S2 (real space coordinates) of the second X-ray tube 110.

Step S611

The three-dimensional position calculation unit 143 calculates the three-dimensional position of the feature part of the treatment tool from a positional relationship between the two straight lines L1 and L2 by using Expressions 1 and 2.

Step S612

The three-dimensional position calculation unit 143 displays the calculated current three-dimensional position of the feature part of the treatment tool, for example, as in a three-dimensional image 702 of FIG. 6. As a result, on a display screen of the display unit 160, a first X-ray image 701 and the three-dimensional image 702 showing the positions of the feature part of the treatment tool in time series are displayed side by side. The operator can understand a projection image of the subject 101 and the treatment tool from the first X-ray image 701, and can understand a temporal change of a depth of the distal end of the treatment tool from the three-dimensional image 702.

Step S613

An instruction to continue the imaging from the operator is checked, and in a case in which the imaging is to be continued, the process returns to step S601, the imaging with the first X-ray tube 60 is continued, the imaging with the second X-ray tube 110 of steps S606 to S610 is performed at regular time intervals, the position of the feature part of the treatment tool is calculated, and the display is updated. As a result, the positions of the feature part of the treatment tool are acquired in time series at regular time intervals.

As described above, the X-ray imaging apparatus 1 according to the present embodiment comprises the second X-ray tube 110, can move the second X-ray tube 110 along the circular orbit 111 around the first X-ray tube 60, and can image the device by the second X-ray tube 110 in a direction in which the treatment tool (device) does not overlap with a bone or other organs while performing the imaging from the first X-ray tube 60 during a medical operation. Therefore, although the X-ray imaging apparatus 1 according to the present embodiment has a simple configuration, it is possible to understand the three-dimensional position of the feature part of the treatment tool in real time.

In addition, in the flow of FIG. 5, since the first X-ray image and the second X-ray image are displayed on the display unit 160 as shown in (b) and (c) of FIG. 4 after executing steps S601, S602, S606, and S607, before the position of the device is calculated, the user can refer to the first and second X-ray images obtained by imaging the device in a plurality of directions, and can understand the position or the direction of the treatment tool (device).

In the above-described embodiment, the extraction of the feature part of the device with respect to the first X-ray image in steps S603 to S605 is executed before or in parallel with the capturing of the second X-ray image by the second X-ray tube 110 in steps S606 and S607, but steps S603 to S605 may be executed after steps S606 and S607.

In addition, as the second X-ray tube 110, a small X-ray tube having small output and a narrow irradiation range can be used, and moreover, the second X-ray tube 110 can be moved along the circular orbit 111, so that the second X-ray tube 110 does not interfere with the capturing of the first X-ray tube 60 or the operator. Therefore, it is possible to perform the imaging in real time during the medical operation by the first X-ray tube 60 and the second X-ray tube 110.

Embodiment 2

An X-ray imaging apparatus according to Embodiment 2 will be described with reference to FIG. 7.

In the X-ray imaging apparatus according to Embodiment 2, the first X-ray tube 60 is directly supported by the first X-ray support arm 90, and the support shaft 132 is installed upright on the upper surface of the first X-ray support arm 90. The base 131a of the arm 131 rotates around the support shaft 132. As a result, the second X-ray tube 110 can be caused to move rotationally along the circular orbit 111.

Since other structures and operations are the same as the structures and operations in Embodiment 1, the description thereof will be omitted.

Embodiment 3

An X-ray imaging apparatus according to Embodiment 3 will be described with reference to FIG. 8.

The X-ray imaging apparatus according to Embodiment 3 comprises a plurality of second X-ray tubes 110. Each of the plurality of second X-ray tubes 110 has a structure in which the second X-ray tubes 110 is rotated around the support shaft 132 by a plurality of arms 131. The plurality of second X-ray tubes 110 may be disposed at symmetrical positions or at asymmetric positions with the first X-ray tube 60 interposed therebetween.

In the X-ray imaging apparatus according to Embodiment 3, since the target part and the treatment tool (device) can be imaged from a plurality of directions by the plurality of second X-ray tubes 110, a larger amount of information can be acquired.

The support shaft 132 may be provided below the first X-ray support arm 90 as in Embodiment 1, or may be provided above the first X-ray support arm 90 as in Embodiment 2.

Since other configurations and operations are the same as the configurations and operations in Embodiment 1, the description thereof will be omitted.

Embodiment 4

An X-ray imaging apparatus 2 according to Embodiment 4 has a function of generating a two-dimensional projection image in a direction desired by the operator from a three-dimensional image captured in advance by a CT apparatus, an MRI apparatus, or the like, and displaying the position of the feature part of the treatment tool on the generated two-dimensional projection image.

Since other configurations of the X-ray imaging apparatus 2 are the same as the configurations in Embodiment 1, the description of the same configurations and the same operations as the configurations and operations of Embodiment 1 will be omitted.

FIG. 9 is a block diagram showing a configuration of main units of the X-ray imaging apparatus 2 according to Embodiment 4. (a) to (c) of FIG. 10 are diagrams showing that a pre-captured three-dimensional image is projected to generate the two-dimensional projection image.

The X-ray imaging apparatus 2 has substantially the same configuration as the X-ray imaging apparatus 1 according to Embodiment 1, but has a difference from Embodiment 1 in that a three-dimensional image acquisition unit 144, a two-dimensional projection image creation unit 145, and an image registration unit 146 are provided in the operation unit 140. The three-dimensional image acquisition unit 144 is connected to an external medical image server 170. The medical image server 170 stores a three-dimensional image of the subject 101 captured in advance by the CT apparatus or the MRI apparatus.

An operation of the X-ray imaging apparatus 2 will be described with reference to the flow of FIG. 11.

The flow of FIG. 11 is a configuration in which steps S801 to S808 and S809 are added to the flow of FIG. 5 of Embodiment 1.

Step S600

First, in step S600 of the flow of FIG. 5 of Embodiment 1, the user disposes of the first X-ray tube 60, and based on prior information of the target part and/or the device to be used, the user moves the second X-ray tube 110 along the circular orbit 111, disposes the second X-ray tube 110 at a position at which the distal end of the device to be inserted can be imaged in a direction that does not overlap with a bone, such as a spine, or an organ, such as a liver.

Step S801

Next, the three-dimensional image acquisition unit 144 acquires the three-dimensional image captured in advance for the subject 101 from the medical image server 170.

Step S802

The subject 101 is irradiated with the X-rays from the first X-ray tube 60, and the X-ray image generation unit 141 acquires the first X-ray image.

Step S803

As shown in (a) of FIG. 10, the two-dimensional projection image creation unit 145 disposes a simulated first X-ray tube 60 and a simulated X-ray detector 70 with respect to the pre-captured three-dimensional image at the same position as the positional relationship between the first X-ray tube 60 and the X-ray detector 70 in step S802, projects the pre-captured three-dimensional image onto the simulated X-ray detector 70, and calculate a first two-dimensional projection image.

Step S804

As shown in (b) of FIG. 10, the image registration unit 146 compares the first X-ray image acquired in step S802 with the first two-dimensional projection image calculated in step S803. In a case in which the first X-ray image and the first two-dimensional projection image are different from each other, the position of the pre-captured three-dimensional image with respect to the simulated first X-ray tube 60 and the simulated X-ray detector 70 is changed, the first two-dimensional projection image is calculated again, and the comparison with the first X-ray image acquired in step S802 is performed. The comparison is repeated until the first X-ray image acquired in step S802 and the first two-dimensional projection image calculated in step S803 match.

Step S805

Next, the subject 101 is irradiated with the X-rays from the second X-ray tube 110, and the X-ray image generation unit 141 acquires the second X-ray image.

Step S806

As shown in (a) of FIG. 10, the two-dimensional projection image creation unit 145 disposes a simulated second X-ray tube 110 and the simulated X-ray detector 70 with respect to the pre-captured three-dimensional image at the same position as the positional relationship between the second X-ray tube 110 and the X-ray detector 70 in step S805, projects the pre-captured three-dimensional image onto the simulated X-ray detector 70, and calculate a second two-dimensional projection image.

Step S807

As shown in (c) of FIG. 10, the image registration unit 146 compares the second X-ray image acquired in step S805 with the second two-dimensional projection image calculated in step S806. In a case in which the second X-ray image and the second two-dimensional projection image are different from each other, the position of the pre-captured three-dimensional image with respect to the simulated second X-ray tube 110 and the simulated X-ray detector 70 is changed, the second two-dimensional projection image is calculated again, and the comparison with the second X-ray image acquired in step S805 is performed. The comparison is repeated until the second X-ray image acquired in step S805 and the second two-dimensional projection image calculated in step S806 match.

Step S808

The image registration unit 146 calculates a parameter for associating the coordinate system of the pre-captured three-dimensional image with the real space coordinates from the position of the pre-captured three-dimensional image with respect to the simulated first X-ray tube 60 and the simulated X-ray detector 70 in a case in which the first X-ray image acquired in step S802 and the first two-dimensional projection image calculated in step S803 match (registration). Similarly, the image registration unit 146 calculates a parameter for associating the coordinate system of the pre-captured three-dimensional image with the real space coordinates from the position of the pre-captured three-dimensional image with respect to the simulated second X-ray tube 110 and the simulated X-ray detector 70 in a case in which the second X-ray image acquired in step S805 and the second two-dimensional projection image calculated in step S806 match (registration). Here, since the parameter obtained from the first X-ray image and the parameter obtained from the second X-ray image are obtained, a parameter for associating the coordinate system of the pre-captured three-dimensional image with the real space coordinates is obtained by selecting any one of the parameters or obtaining an average.

Steps S601 to S612

Steps S601 to S612 are executed in the same manner as in Embodiment 1, the current three-dimensional position of the feature part of the treatment tool is calculated, and the three-dimensional image 702 indicating the calculated position and the first X-ray image 701 are displayed on the display unit 160.

Step S809

The pre-captured three-dimensional image is converted into the real space coordinates by using the parameter for associating the coordinate system of the pre-captured three-dimensional image obtained in step S808 with the real space coordinates, and then the two-dimensional projection is performed in a direction desired by the operator to calculate a computational projection image 703. The position of the feature part of the treatment tool calculated in step S611 is overlapped on the calculated computational projection image 703, and is displayed as shown in FIG. 12.

With the X-ray imaging apparatus 2 according to Embodiment 4, the position of the feature part of the treatment tool recognized in real time can be shown on the two-dimensional projection image obtained by projecting the pre-captured three-dimensional image in the direction designated by the operator, and the correspondence between the position of the feature part of the treatment tool and the anatomical structure of the subject can be easily understood. As in Embodiment 1, steps S603 to S605 in FIG. 11 may be executed after steps S606 and S607.

Embodiment 5

Embodiments 1 to 4 described above have a configuration in which, in step S600, based on prior information of the target part and/or the device to be used, the user moves the second X-ray tube 110 along the circular orbit 111, disposes the second X-ray tube 110 at a position at which the distal end of the device to be inserted can be imaged in a direction that does not overlap with a bone, such as a spine, or an organ, such as a liver.

In Embodiment 5, instead of the user determining the position of the second X-ray tube 110, a configuration is adopted in which the X-ray imaging apparatus moves the second X-ray tube 110 to an appropriate position or prompt the user to move the second X-ray tube 110 to an appropriate position.

For example, in a case in which a tumor is described as an example as a target as shown in FIG. 13A, in a case in which the tumor is located at a position close to a spine extending in a body axis direction, the X-ray imaging apparatus detects the fact by the following detection unit. Specifically, the feature part extraction unit 142 functions as the detection unit, extracts the tumor and the spine from the first X-ray image captured by the first X-ray tube 60 or the second X-ray image captured by the second X-ray tube 110, and checks whether or not the positions of the extracted tumor and spine have an overlap relationship. Alternatively, the user indicates the positions of the tumor and the spine on the first X-ray image or the second X-ray image by using a pointing device or the like, to input the positions of the tumor and the spine as the determination target of "part overlap" to the X-ray imaging apparatus. The X-ray imaging apparatus checks whether or not the positions of the tumor and the spine input from the user have an overlap relationship. In addition, a configuration may be adopted in which the user designates only the position of the tumor by using a pointing device or the like, and the feature part extraction unit 142 extracts the position of the spine.

In a case in which the X-ray imaging apparatus detects that the positions of the tumor and the spine overlap with each other (see FIG. 13B), the display prompts the user to dispose the second X-ray tube 110 at a position where the angle at which the second X-ray tube 110 views the spine is different from the angle at which the first X-ray tube 60 views the spine. In other words, a display prompts the user to position the second X-ray tube 110 in a horizontally shifted manner with respect to the central axis (vertebrae) of the subject 101. The user adjusts the position of the second X-ray tube 110 based on this display. Alternatively, a configuration may be configured in which the user approves that the X-ray imaging apparatus adjusts the position of the second X-ray tube 110. In the latter case, the X-ray imaging apparatus moves the position of the second X-ray tube 110 by a predetermined amount, or moves the second X-ray tube 110 so that the tumor and the spine do not overlap with each other in the second X-ray image.

In a case in which the second X-ray tube 110 is disposed in the left-right direction with respect to the spine, the second X-ray image in which the tumor and the spine do not overlap with each other is obtained (see FIG. 13C). As a result, the distal end of the device to be inserted toward the tumor does not overlap with the spine, and the S/N of the images of the distal end of the device in the first X-ray image and the second X-ray image can be ensured.

Embodiment 6

Although Embodiment 5 has a configuration in which the X-ray imaging apparatus detects whether or not the positions of the tumor and the spine overlap with each other, a configuration may be adopted in which, in a case in which the user views the first X-ray image or the second X-ray image and it is difficult to see the tumor and the spine because the positions of the tumor and the spine overlap with each other, the user presses an "overlap cancellation button" prepared in advance on the screen.

In a case in which the overlap cancellation button is pressed by the user, the X-ray imaging apparatus moves the position of the second X-ray tube 110 by a predetermined amount.

As a result, the second X-ray image in which the tumor and the spine do not overlap with each other can be obtained.

Embodiment 7

In a case in which the treatment tool (device) is inserted and moved by the operator during the procedure, there is a possibility that the device may come out of the image by the second X-ray tube 110 (second X-ray image). Then, as a result of extracting the feature part of the device by the feature part extraction unit 142, in a case in which the position is in a region within 10% from, for example, an edge of a field of view of the second X-ray image, the operation unit 140 may perform the following operation.

For example, the operation unit 140 displays the display prompting the user to move the position of the second X-ray tube 110, and the user moves the position of the second X-ray tube 110 along the circular orbit 111, whereby the feature part enters the field of view of the second X-ray image. Alternatively, the operation unit 140 instructs the drive controller 151 to move the position of the second X-ray tube 110 by a predetermined amount along the circular orbit 111, whereby the feature part enters in the field of view of the second X-ray image. In the latter case, the operation unit 140 may check with the user whether or not to change the position of the second X-ray tube 110 before moving the position of the second X-ray tube 110.

The operation unit 140 may change the position of the second X-ray tube 110 by the movement along the circular orbit 111 and expanding and contracting the arm 131 by the expansion and contraction mechanism 134, in addition to moving the second X-ray tube 110 along the circular orbit 111.

That is, in Embodiment 7, the operation unit 140 drives the rotation mechanism 133 to move the second X-ray tube 110 in accordance with the position of the feature part included in the second X-ray image, thereby causing the field of view of the second X-ray image to track the movement of the feature part.

Embodiment 8

An X-ray imaging apparatus according to Embodiment 8 has the same configuration as in Embodiments 1 to 4, but further comprises a grid in which a plurality of protruding lines disposed on the X-ray detector are arranged in parallel, and a rotation driving unit that rotates the grid in the principal plane. The rotation driving unit rotates the grid in accordance with the position of the second X-ray tube on the circular orbit.

The grid has an action of reducing scattered rays on the X-ray detector, but the S/N of the X-ray detector is reduced depending on the position of the second X-ray tube 110 on the circular orbit 111.

Specifically, as shown in FIGS. 14A and 14B, in a case in which the optical axis (X-ray irradiation direction) of the second X-ray tube 110 intersects with the longitudinal direction of the protruding lines of the grid, a shadow of the grid is remarkably generated on the X-ray detector 70, and the S/N of the output of the X-ray detector 70 is reduced. Therefore, as shown in FIG. 14C, the S/N can be maintained by rotating the grid so that the optical axis of the second X-ray tube 110 is parallel to the longitudinal direction of the protruding lines of the grid.

Specifically, the rotation driving unit includes a mechanism unit that rotates the grid in the principal plane in the top plate 40. The rotation driving unit may rotate the grid in synchronization with the rotational movement of the second X-ray tube 110.

In addition, after detecting that the position of the second X-ray tube 110 is fixed (the fluctuation in the positional information is eliminated) via the drive controller 151, the rotation driving unit may automatically rotate the grid based on the positional information of the second X-ray tube 110.

In addition, the user may manually rotate the grid after manually rotating the second X-ray tube 110.

EXPLANATION OF REFERENCES

1: X-ray imaging apparatus
2: X-ray imaging apparatus
10: stand
20: column support arm
30: support frame
40: top plate
50: column
51: first slide mechanism
52: second slide mechanism
53: first rotation mechanism
60: first X-ray tube
61: axis
70: X-ray detector
90: first X-ray support arm
101: subject
110: second X-ray tube
111: circular orbit
120: first support portion
130: second support portion
131: arm
132: support shaft
133: rotation mechanism
134: expansion and contraction mechanism
140: operation unit
141: X-ray image generation unit
142: feature part extraction unit
143: three-dimensional position calculation unit
144: three-dimensional image acquisition unit
145: two-dimensional projection image creation unit
146: image registration unit
150: operation controller
151: drive controller
152: output controller
153: high-voltage generator
154: data collection unit
160: display unit
170: medical image server
223: raising and laying mechanism
224: moving mechanism
701: first X-ray image
702: three-dimensional image
703: computational projection image

What is claimed is:

1. An X-ray imaging apparatus comprising:
   a top plate on which a subject is placed;
   a first X-ray tube that irradiates the subject with X-rays;

a first support portion that supports the first X-ray tube;

a second X-ray tube that irradiates the subject with X-rays;

a second support portion that supports the second X-ray tube;

an X-ray detector that detects the X-rays that are applied from the first X-ray tube and the second X-ray tube and are transmitted through the subject; and a processor configured to acquire a first X-ray image from output of the X-ray detector that has detected the X-rays applied from the first X-ray tube, acquires a second X-ray image from output of the X-ray detector that has detected the X-rays applied from the second X-ray tube, and uses a position of an image of a predetermined feature part included in the first X-ray image and a position of an image of the feature part included in the second X-ray image to calculate a three-dimensional position of the image of the predetermined feature part, and the second support portion includes a mechanism that supports the second X-ray tube in a rotationally movable manner along a circular orbit about an axis connecting the first X-ray tube and the top plate, wherein the second support portion includes a mechanism unit that changes a radius of the circular orbit, and a maximum irradiation region of the X-rays from the second X-ray tube to the X-ray detector is smaller than a maximum irradiation region of the X-rays from the first X-ray tube to the X-ray detector.

2. The X-ray imaging apparatus according to claim 1, wherein the second support portion includes an arm having a base and a distal end, a support shaft, and a rotation mechanism, the support shaft is provided at a position on the first support portion that supports the first X-ray tube, the base of the arm is supported by the support shaft, the second X-ray tube is provided at the distal end of the arm, and the support shaft is provided with the rotation mechanism that rotates the base of the arm about the support shaft.

3. The X-ray imaging apparatus according to claim 2, wherein the arm is provided with an expansion and contraction mechanism that changes a radius of the circular orbit by expanding and contracting the arm in an axial direction.

4. The X-ray imaging apparatus according to claim 1, wherein the second support portion is provided with a driving unit that changes a position of the second X-ray tube along the circular orbit.

5. The X-ray imaging apparatus according to claim 4, wherein the operation unit drives the driving unit to move the second X-ray tube in accordance with the position of the image of the feature part included in the second X-ray image, and causes a field of view of the second X-ray image to track movement of the feature part.

6. The X-ray imaging apparatus according to claim 1, further comprising:

a third X-ray tube that irradiates the subject with X-rays; and a third support portion that supports the third X-ray tube, wherein the third support portion supports the third X-ray tube in a rotationally movable manner along the circular orbit about an axis passing through the first X-ray tube.

7. The X-ray imaging apparatus according to claim 1, wherein maximum output of the X-rays from the second X-ray tube is smaller than maximum output of the X-rays from the first X-ray tube.

8. The X-ray imaging apparatus according to claim 1, wherein the operation unit includes an extraction unit that extracts and detects the images of the predetermined feature part included in the first X-ray image and the second X-ray image, and a three-dimensional position calculation unit that calculates a three-dimensional position of the feature part by using the positions of the images of the feature part included in the first X-ray image and the second X-ray image.

9. The X-ray imaging apparatus according to claim 1, wherein the operation unit detects positions of a predetermined target and a spine included in the first X-ray image or the second X-ray image or receives the positions of the target and the spine from a user, and displays, on a display unit, display prompting disposition of the second X-ray tube at a position shifted from a central axis of the subject in a left-right direction in a case in which the positions of the target and the spine overlap with each other.

10. The X-ray imaging apparatus according to claim 1, further comprising:

a grid in which a plurality of protruding lines disposed on the X-ray detector are arranged in parallel; and a rotation driving unit that rotates the grid in a principal plane, wherein the rotation driving unit rotates the grid in accordance with a position of the second X-ray tube on the circular orbit.

11. An X-ray imaging method comprising:

disposing a first X-ray tube, supported by a first support portion, at a position at which a target part of a subject placed on a top plate is irradiated with X-rays, and disposing a second X-ray tube, supported by a second support portion, by causing the second X-ray tube to move rotationally along a circular orbit about an axis connecting the first X-ray tube and the top plate;

acquiring a first X-ray image by irradiating the subject with the X-rays from the first X-ray tube and detecting the X-rays transmitted through the subject by an X-ray detector;

acquiring a second X-ray image by irradiating the subject with X-rays from the second X-ray tube and detecting the X-rays transmitted through the subject by the X-ray detector; and using a position of an image of a predetermined feature part included in the first X-ray image and a position of an image of the feature part included in the second X-ray image to calculate a three-dimensional position of the image of the predetermined feature part, wherein the second support portion includes a mechanism unit that changes a radius of the circular orbit, and a maximum irradiation region of the X-rays from the second X-ray tube to the X-ray detector is smaller than a maximum irradiation region of the X-rays from the first X-ray tube to the X-ray detector.

* * * * *